US012605321B2

(12) United States Patent
Cruz et al.

(10) Patent No.: US 12,605,321 B2
(45) Date of Patent: Apr. 21, 2026

(54) PERSONAL CARE COMPOSITIONS

(71) Applicant: Colgate-Palmolive Company, New York, NY (US)

(72) Inventors: Luis Alberto Cruz, Del.Miguel Hidalgo (MX); Arturo Zuniga, Del Miguel Hidalgo (MX); Changlong Chen, New Brunswick, NJ (US); Hongwei Shen, Holmdel, NJ (US); Komal Shahani, Edison, NJ (US); Nadia Soliman, East Brunswick, NJ (US); Amira Khan, East Windsor, NJ (US)

(73) Assignee: Colgate-Palmolive Company, New York, NY (US)

( * ) Notice: Subject to any disclaimer, the term of this patent is extended or adjusted under 35 U.S.C. 154(b) by 109 days.

(21) Appl. No.: 17/216,148

(22) Filed: Mar. 29, 2021

(65) Prior Publication Data

US 2021/0299020 A1     Sep. 30, 2021

Related U.S. Application Data

(60) Provisional application No. 63/001,757, filed on Mar. 30, 2020.

(51) Int. Cl.

| | |
|---|---|
| *A61K 8/46* | (2006.01) |
| *A61K 8/362* | (2006.01) |
| *A61K 8/365* | (2006.01) |
| *A61K 8/73* | (2006.01) |
| *A61Q 5/02* | (2006.01) |
| *A61Q 5/12* | (2006.01) |
| *A61Q 19/10* | (2006.01) |
| *A61Q 90/00* | (2009.01) |

(52) U.S. Cl.
CPC .............. *A61K 8/466* (2013.01); *A61K 8/362* (2013.01); *A61K 8/365* (2013.01); *A61K 8/73* (2013.01); *A61Q 5/02* (2013.01); *A61Q 5/12* (2013.01); *A61Q 19/10* (2013.01); *A61Q 90/00* (2013.01); *A61K 2800/28* (2013.01); *A61K 2800/30* (2013.01); *A61K 2800/524* (2013.01); *A61K 2800/5426* (2013.01); *A61K 2800/596* (2013.01)

(58) Field of Classification Search
None
See application file for complete search history.

(56) References Cited

U.S. PATENT DOCUMENTS

| | | |
|---|---|---|
| 5,175,000 A | 12/1992 | Godowski et al. |
| 5,443,817 A | 8/1995 | Rosser et al. |
| 5,641,480 A | 6/1997 | Vermeer |
| 7,157,413 B2 | 1/2007 | Lazzeri et al. |
| 7,326,775 B2 | 2/2008 | Naidu |
| 7,901,696 B2 | 3/2011 | Eknoian et al. |
| 7,928,087 B2 | 4/2011 | Fack et al. |
| 8,343,902 B2 | 1/2013 | Walters et al. |
| 9,271,908 B2 | 3/2016 | Allef et al. |
| 9,320,697 B2 | 4/2016 | Kleinen et al. |
| 9,877,906 B2 | 1/2018 | Doi et al. |
| 9,949,915 B2 | 4/2018 | Rubin et al. |
| 9,993,408 B2 | 6/2018 | Fevola et al. |
| 10,188,112 B2 | 1/2019 | Arvanitidou et al. |
| 10,561,592 B2 | 2/2020 | Darras et al. |
| 10,695,285 B2 | 6/2020 | Leclere |
| 2004/0057874 A1 | 3/2004 | Ishiguro |
| 2008/0187502 A1 | 8/2008 | Garay et al. |
| 2013/0017243 A1 | 1/2013 | Shi et al. |
| 2017/0319453 A1 | 11/2017 | Ando |
| 2018/0016524 A1 | 1/2018 | Dong et al. |
| 2018/0016525 A1 | 1/2018 | Scheuermann et al. |
| 2018/0098923 A1 | 4/2018 | Hutton, III |
| 2018/0311127 A1 | 11/2018 | Padyachi et al. |
| 2019/0000902 A1 | 1/2019 | Leclere-Bienfait et al. |
| 2019/0021971 A1 | 1/2019 | Schroeder et al. |
| 2019/0262248 A1 | 8/2019 | Youssef et al. |
| 2019/0365623 A1 | 12/2019 | Botto et al. |

FOREIGN PATENT DOCUMENTS

| | | |
|---|---|---|
| CN | 102686715 A | 9/2012 |
| CN | 107427438 A | 12/2017 |
| CN | 108697610 A | 10/2018 |
| EP | 1353631 | 9/2011 |
| EP | 2468842 | 6/2012 |
| EP | 2277860 | 8/2015 |
| EP | 2932959 | 10/2015 |
| EP | 3061442 | 8/2016 |
| EP | 3260171 | 12/2017 |
| ES | 2349855 | 1/2011 |
| FR | 3029778 | 6/2016 |
| GB | 2172298 | 9/1986 |
| WO | 2011/049932 A1 | 4/2011 |
| WO | 2015/079026 | 6/2015 |
| WO | 2016/092189 | 6/2016 |
| WO | 2019/170249 | 9/2019 |
| WO | 2019/193109 | 10/2019 |
| WO | 2020/023187 | 1/2020 |

OTHER PUBLICATIONS

Handbook of Detergents, CRC Press, (2009 by Uri Zoller), pp. 287-293.
Bioelements, USA, 2019, "Urban Undo Cleanser", Mintel Database GNPD AN: 6889243.
Change Look, 2018, "Botanic Active Gel", Mintel Database GNPD AN: 6044749.
International Search Report and the Written Opinion of the International Searching Authority Application PCT/US2021/024692 mailed Jul. 19, 2021.
International Search Report and the Written Opinion of the International Searching Authority issued in International Application PCT/US2021/070333 mailed Jul. 27, 2021.

(Continued)

*Primary Examiner* — Anna R Falkowitz
*Assistant Examiner* — Garen Gotfredson

(57) ABSTRACT

Described herein are personal care compositions comprising a sulfate-free surfactant system and a preservative system comprising an organic acid; along with methods of making and using same.

19 Claims, 4 Drawing Sheets

(56) References Cited

OTHER PUBLICATIONS

Productos Familia, 2019, "Intimate Soap," Mintel Database GNPD AN: 6915113.

Rembiesa et al., 2018, "The impact of pollution on skin and proper efficacy testing for anti-pollutions claims," Cosmetics 5,4.

Bio-Terge As-40, Product Bulletin, Stepan, Aug. 2012, pp. 1-2.

Pluracare L/F Grades Ploxamer: Technical Information, BASF The Chemical Company, Personal Care, Jul. 2009, pp. 1-10.

Pendergrass, K. et al., "Should Xanthan Gum be allowed in Grain-Free, Paleo, and Keto Certified Standards?" Microbiome Diet Research, (Dec. 2019) The Paleo Foundation Research Review, pp. 1-11.

Niziol-Lukaszewska Z. et al.: "Inulin as an Effectiveness and Safe Ingredient in Cosmetics", Polish Journal of Chemical Technology, 2019, vol. 21, No. 1, pp. 44-49, DOI: 10.2478/pjct-2019-0008.

O'Lenick, T., Surfactant Spectator, SurfaTech Corporation, Jun. 2009, vol. 1 No. 3. (Year: 2009).

PERSONAL CARE COMPOSITIONS

BACKGROUND

Personal care compositions often contain sulfate-based surfactants, such as sodium lauryl sulfate, sodium lauryl ether sulfate, ammonium lauryl sulfate, and ammonium laureth sulfate. These sulfate-based surfactants facilitate the cleansing process by decreasing the surface tension of water and thus allowing water to adhere to dirt on the skin or hair. However, there is increasing consumer concern that sulfate containing surfactants may strip the skin and hair of its natural oils, thereby leading to over-drying. As such, there is continuing demand for personal care compositions that are free of sulfate-containing surfactants and/or incorporate milder surfactants which do not cause over-drying of skin and hair.

Use of sulfate-free cleansers has been unsuccessful because formulations are difficult to thicken sufficiently to afford good sensory properties, especially when lipophilic or oily ingredients are incorporated. Additionally, such sulfate-free formulations effect poor solubilization of fragrances and oils. Traditionally, either thickening polymers, such as acrylic acid and hydroxypropyl guar, are used to create a structured backbone to maintain a good rheological profile. Such cleansers with poor thickening qualities do not remain on the hair or skin during and/or after application, and can drip and run into the user's eyes, mouth, ears or nasal passages. This lends to an unpleasant consumer experience. Current market solutions for avoiding sulfate-based surfactants introduce excessive product cost and/or loss of aesthetic and functional properties of the shampoo or gel.

There is a need to produce sulfate-free personal care compositions which maintain adequate thickness and do not introduce excessive costs for the product.

Use of the surfactants alpha olefin sulfonate (AOS) and cocamidopropyl betaine (CAPB) have been reported previously, however, these teachings disclosed the additional need for use of thickening agents, such as acrylic acid (Carbomer), polyethylene glycol, and cocamide MEA, to be added to build viscosity in reported formulations.

In some embodiments, the present invention solves these previous technical problems in relation to sulfate-free liquid detergents. More particularly, it relates to personal care compositions for cleansing and/or conditioning human hair and skin.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

Applicants have discovered sulfate-free liquid personal care formulations comprising a preservative system comprising an organic acid and a sulfate-free surfactant system comprising an anionic surfactant and an amphoteric surfactant. In certain embodiments, such formulations surprisingly do not require an additional need for thickener.

In at least one embodiment, the present invention is directed to a personal care composition comprising: a cosmetically acceptable carrier; a preservative system comprising an organic acid; and a sulfate-free surfactant system comprising an anionic surfactant and an amphoteric surfactant.

In certain embodiments, the anionic surfactant is selected from: a taurate; a succinate; a sarcosinate; an isethionate; a carboxylate; a lactylate; a glutamate; a glycinate; a sulfoacetate; and a sulfonate surfactant. In certain embodiments, the anionic surfactant is selected from: sodium n-methyl-n-oleyl taurate; sodium cocoyl isethionate; sodium capryloyl isethionate; sodium caproyl isethionate; sodium lauroyl isethionate; sodium palmitoyl isethionate; sodium diisobutyl sulfosuccinate; sodium diamyl sulfosuccinate; di-N-hexyl sodium sulfosuccinate; disodium lauryl sulfosuccinate; disodium laureth sulfosuccinate; disodium PEG-12 dimethicone sulfosuccinate; sodium oleyl sarcosinate; sodium laurate; sodium myristate; sodium palmitate; sodium stearate; sodium lauroyl lactylate; sodium palmitoyl lactylate; sodium stearoyl lactylate; sodium cocoyl glutamate; disodium cocoyl glutamate; sodium lauroyl glycinate; sodium lauryl sulfoacetate; stearyltoluene sodium sulfonate; sodium diamyl sulfosuccinate; sodium pentanesulfonate; a linear alkyl benzene sulfonate (e.g. sodium dodecylbenzenesulfonate or ammonium dodecylbenzenesulfonate); sodium 1-butanesulfonate; sodium lignosulfonate; sodium n-octyl sulfonate; an alpha olefin sulfonate; and a combination of two or more thereof. In certain embodiments, the anionic surfactant comprises an alpha olefin sulfonate.

In certain embodiments, the amphoteric surfactant is selected from: $C_{12-14}$ alkyl betaine; $C_{12-18}$ alkyl betaine; $C_{14-15}$ hydroxysulfo betaine; cocoamidopropyl betaine; cocoamidopropyl sultaine; lauroamphoglycinate; dihydroxyethyl tallow glycinate; isostearoamphopropionate; dodecyl betaine; tetradecyl betaine; hexadecyl betaine; sodium acylamphopropionate; disodium acyldiamphopropionate; sodium lauroamphoacetate; cocoamphodiacetate; $C_{12-18}$ alkylampho propionate; $C_{12}$ alkyliminodipropionate; and a combination of two or more thereof. In certain embodiments, the amphoteric surfactant comprises cocamidopropyl betaine.

In certain embodiments, the organic acid is selected from: citric acid; lactic acid; acetic acid; formic acid; oxalic acid; uric acid; malic acid; and a combination of two or more thereof. In certain embodiments, the organic acid comprises lactic acid.

In certain embodiments, the personal care contains a weight ratio of amphoteric surfactant to anionic surfactant from about 0.5:1 to about 6:1, optionally from about 0.55:1 to about 5.8:1, further optionally from about 0.58:1 to about 5.6:1.

In certain embodiments, the amphoteric surfactant comprises cocamidopropyl betaine and the anionic surfactant comprises an alpha olefin sulfonate. In certain embodiments, the active alpha olefin sulfonate is present in an amount between 1 to 15 wt. %, 2 to 12 wt. %, 3 to 10 wt. %, of the total weight of the personal care composition. In further embodiments, the active amphoteric surfactant is present in an amount between 2 to 10 wt. %, 2 to 8 wt. %, 3 to 8 wt. %, or 4 to 8 wt. %, of the total weight of the personal care composition.

In certain embodiments, the active organic acid is present in an amount of from about 0.3 to about 2 wt. %, from about 0.3 to about 1 wt. %, or from about 0.3 to about 0.8 wt. %.

In certain embodiments, the personal care composition further comprises sodium benzoate. In certain embodiments, the active sodium benzoate is present in an amount of from about 0.1 wt. % to about 1 wt. %.

In certain embodiments, the personal care composition further comprises sodium lauroyl sarcosinate. In certain embodiments, the sodium lauroyl sarcosinate is present in an amount of from about 0.2 wt. % to about 1.5 wt. %.

In certain embodiments, personal care composition further comprises a humectant selected from: glycerin; butyloctanol; hyaluronic acid; urea; sodium lactate; propylene glycol; glycolic acid; sorbitol; and a combination of two or more thereof. In certain embodiments, the humectant is selected from: glycerin; butyloctanol; and a combination thereof. In certain embodiments, the butyloctanol is present in an amount of from about 0.005 wt. % to about 0.5 wt. %, optionally from about 0.01 wt. % to about 0.1 wt. %, further optionally 0.01 wt. % or 0.05 wt. %.

In certain embodiments, the personal care composition is substantially free of thickening polymers.

In certain embodiments, the personal care composition has a pH of from about 3.5 to about 10.0. In other embodiments, the personal care composition has a pH of from about 3.5 to about 8.0. In some embodiments, the personal care composition has a pH of from about 3.5 to about 7.5. In other embodiments, the personal care composition has a pH of from about 3.5 to about 7.0. In further embodiments, the personal care composition has a pH of from about 3.5 to about 6.5. Still other embodiments provide personal care compositions having a pH of from about 3.5 to about 6.0. While other embodiments provide personal care compositions having a pH of from about 3.5 to about 5.5. Yet other embodiments provide personal care compositions having a pH of from about 3.5 to about 5.0. In certain embodiments, the personal care composition has a pH of from about 3.75 to about 4.5.

In certain embodiments, the personal care composition has a viscosity of from about 2,000 centipoise (cP) to about 20,000 cP, or about 3,000 cP to about 16,000 cP, or about 4,000 cP to about 12,000 cP, including all values in between these ranges.

In certain embodiments, the personal care composition is substantially free of a sulfate-containing surfactant. In certain embodiments, the personal care composition is free of a sulfate-containing surfactant.

In certain embodiments, the personal care composition further comprises a cationic polymer. In certain embodiments, the cationic polymer provides conditioning benefits. In certain embodiments, the cationic comprises polymer a copolymer of acrylamide and diallyldimethylammonium chloride.

In certain embodiments, the personal care composition further comprises a prebiotic polysaccharide. In certain embodiments, the prebiotic polysaccharide comprises a fructan. In other embodiments, the prebiotic polysaccharide comprises inulin. In certain embodiments, the prebiotic polysaccharide is present in an amount of from about 0.1 wt. % to about 5 wt. %, optionally from about 0.5 wt. % to about 3 wt. %, further optionally about 2 wt. %.

In certain embodiments, the personal care composition further comprises an ingredient selected from: caprylyl glycol; a metal ion source (e.g., a zinc ion source); an emollient (e.g., glyceryl oleate); a PEO-PPO block copolymer; sodium PCA; a fragrance; a colorant; an antioxidant (e.g., tocopherol); and a combination of two or more thereof.

In certain embodiments, the personal care composition is in a form selected from: a hand soap, a body wash, a face wash, a shower gel, a shampoo, a conditioner, a cleanser, an exfoliating scrub, and a facial scrub.

In at least one embodiment, the present invention is directed to a personal care composition comprising: a surfactant system consisting essentially of: a betaine-type surfactant and a sulfonate surfactant; optionally a prebiotic polysaccharide; and a cationic polymer; wherein the composition is substantially free of a thickening agent. In certain embodiments, the betaine-type surfactant comprises cocamidopropyl betaine. In certain embodiments, the sulfonate surfactant comprises an alpha olefin sulfonate.

In at least one embodiment, the present invention is directed to a method of treating, preventing or ameliorating a symptom associated with a disease, disorder or condition of a keratinous substance, comprising applying a personal care composition according to any foregoing claim to a keratinous substance of a subject in need thereof.

In at least one embodiment, the present invention is directed to a method of cleansing a keratinous substance comprising applying a personal care composition according to any foregoing claim to a keratinous substance of a subject in need thereof. In certain embodiments, the keratinous substance is selected from: skin, hair, nails, and a combination of two or more thereof. In certain embodiments, the method further comprises rinsing the personal care composition from the keratinous substance to which it is applied.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

Figure 1:
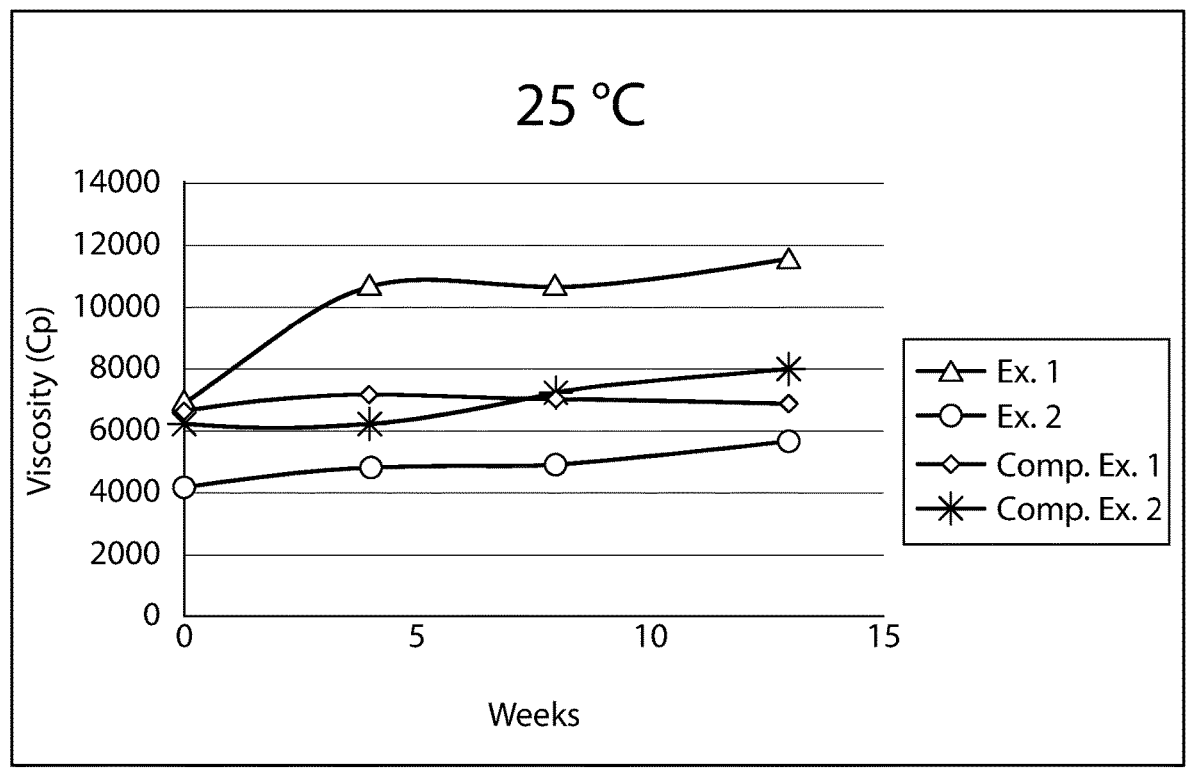
FIG. 1 depicts the change in viscosity of various formulations at 25° C. over a period of about 13 weeks.

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other applications and methods. It is to be understood that the invention is not limited in its application to the details of any particular embodiment shown. The terminology used herein is for the purpose of description and not to limit the invention, its application, or uses.

As used herein and in the appended claims, the singular forms "a", "an", and "the" include plural references unless the context dictates otherwise. The singular form of any class of the ingredients refers not only to one chemical species within that class, but also to a mixture of those chemical species. The terms "a" (or "an"), "one or more" and "at least one" may be used interchangeably herein. The terms "comprising", "including", and "having" may be used interchangeably. The term "include" should be interpreted as "include, but are not limited to". The term "including" should be interpreted as "including, but are not limited to".

As used throughout, ranges are used as shorthand for describing each and every value that is within the range. Any value within the range can be selected as the terminus of the range.

Unless otherwise specified, all percentages and amounts expressed herein and elsewhere in the specification should be understood to refer to percentages by weight. Unless otherwise specified, the amounts given are based on the active weight of the material. According to the present application, the term "about" means+/−5% of the reference value. As used herein, the term "substantially free" is intended to mean an amount less than about 1 wt. %; preferably less than about 0.5 wt. %, and more preferably less than about 0.25 wt. % of the composition.

Unless defined otherwise, all technical and scientific terms used herein have the same meanings as commonly understood by one of ordinary skill in the art to which this invention belongs. All patents, patent applications, publications, and other references cited or referred to herein are incorporated by reference in their entireties for all purposes. In the event of a conflict in a definition in the present disclosure and that of a cited reference, the present disclosure controls.

Personal care compositions include hair care, skin care, sun care, facial care, and nail care compositions. In some embodiments, the personal care composition may be a liquid cleansing composition. In some embodiments, the personal care composition is applied to the person's skin or scalp. Examples of personal care compositions include an antiperspirant, a deodorant, a body wash, face wash, a shower gel, a lotion, a bar soap, a soft soap, a shampoo, a hair conditioner, a sunscreen, a facial cleanser, a facial toner, an exfoliant, a mask, a serum, a moisturizer, and a cosmetic (e.g. lipstick, concealer, blush, eye shadow, etc.). The personal care composition may be defined, classified and/or regulated by national or international regulatory agencies as a cosmetic, or as a drug.

A deodorant is a composition that is applied to the body of a person to prevent body odor caused by the bacterial breakdown of perspiration. A deodorant may be applied to any part of the body. Under selected embodiments, the deodorant is applicable to armpits and feet.

An antiperspirant is a composition that mitigates body odor as well as prevents sweating by affecting sweat glands. An antiperspirant may be applied to any part of the body and are generally applied to the underarms.

A body wash is a liquid product used for cleaning the body during showers. A body wash comprises synthetic detergents derived from either petroleum or plant sources. A body wash has a lower pH value than soap and is typically less drying to the skin than a soap.

Under one embodiment, a shower gel is synonymous with body wash. Under an alternative embodiment, a shower gel has a higher viscosity than body wash and has a firmer consistency. A shower gel may have an ingredient that has a cooling feel.

A lotion is a low-viscosity topical preparation for application to the skin. Lotions are applied to external skin with bare hands, a brush, or a clean cloth. A lotion, such as a hand lotion or a body lotion, provides smoothing, moisturizing, softening and perfuming of the skin. A lotion may be used as a medicine delivery system.

In certain embodiments, the present invention is directed to a personal care product that may be a soap. The soap may be a hand soap and/or body soap.

The term "cosmetically acceptable carrier" as used herein refers to a physiologically acceptable medium which is compatible with keratinous substances. Suitable carriers are well known in the art and are selected based on the end-use application. Preferably, the carriers of the present invention are suitable for application to skin (e.g. in the form of creams, milks, lotions, masks, serums, hydrodispersions, foundations, cream gels, or gels etc.). Such carriers are well-known to one of ordinary skill in the art and can include one or more compatible liquid or solid filler diluent, excipient, adjuvant, additive or vehicle which are suitable for application to skin. In certain embodiments, the cosmetically acceptable carrier further comprises an ingredient selected from: caprylyl glycol; a metal ion source (e.g., a zinc ion source); an emollient (e.g., glyceryl oleate); a PEO-PPO block copolymer; sodium PCA; a fragrance; a colorant; an antioxidant (e.g., tocopherol); and a combination of two or more thereof.

In certain embodiments, the personal care compositions comprise a preservative system comprising an organic acid. Examples of suitable preservatives include benzyl alcohol, piroctone olamine, phenoxyethanol, parabens, pentanediol, benzoic acid/sodium benzoate, sorbic acid/potassium sorbate, and other organic acids used to provide antimicrobial protection. Preservation boosting ingredients include anisic acid, lactic acid, sorbitan caprylate, ethylhexylglycerin, caprylyl glycol, octanediol, and similar substances. Suitable preservatives are the substances listed in the International Cosmetic Ingredient Dictionary and Handbook, 9th Edition with the function "preservatives". In at least one embodiment, the preservative is selected from the group consisting of phenoxyethanol, benzyl paraben, butyl paraben, ethyl paraben, isobutyl paraben, isopropyl paraben, methyl paraben, propyl paraben, iodopropynyl butylcarbamate, methyldibromoglutaronitrile, DMDM hydantoin and combinations thereof. In at least one embodiment, the composition comprises a preservative selected from the group consisting of cetyltrimethyl ammoniumchloride, cetylpyridinium chloride, benzethonium chloride, diisobutylethoxyethyldimethyl benzylammoniumchloride, sodium N-lauryl sarcosinate, sodium-N-palmethylsarcosinate, lauroylsarcosine, N-myristoylglycine, potassium-N-laurylsarcosine, trimethylammoniumchloride, sodium aluminum chlorohydroxylactate, triethylcitrate, tricetylmethylammoniumchloride, 2,4,4'-trichloro-2'-hydroxydiphenylether (Triclosan), phenoxyethanol, 1,5-pentandiol, 1,6-hexandiol, 3,4,4'-trichlorocarbanilide (Triclocarban), diaminoalkylamide, L-lysine hexadecylamide, heavy metal citrate salts, salicylate, piroctose, zinc salts (e.g., zinc oxide, zinc sulfate), pyrithione and its heavy metal salts, zinc pyrithione, zinc phenol sulfate, farnesol, ketoconazol, oxiconazol, bifonazole, butoconazole, cloconazole, clotrimazole, econazole, enilconazole, fenticonazole, isoconazole, miconazole, sulconazole, tioconazole, fluconazole, itraconazole, terconazole, naftifine, terbinafine, selenium disulfide, Octopirox®, methylchloroisothiazolinone, methylisothiazolinone, methyldibromo glutaronitrile, AgCl, chloroxylenol, sodium salts of diethylhexylsulfosuccinate, sodiumbenzoate, phenoxyethanol, benzylalkohol, phenoxyisopropanol, paraben, such as butyl-, ethyl-, methyl- and propylparaben, and their salts, pentandiol, 1,2-octanediol, ethylhexylglycerinw, benzylalcohol, sorbic acid, benzoic acid, lactic acid, imidazolidinyl urea, diazolidinyl urea, dimethylol dimethyl hydantoin (DMDMH), sodium salts of hydroxymethyl glycinate, hydroxyethylglycine of sorbic acid and combinations thereof. In at least one embodiment, the preservative is selected from the group consisting of phenoxyethanol, benzyl paraben, butyl paraben, ethyl paraben, isobutyl paraben, isopropyl paraben, methyl paraben, propyl paraben, iodopropynyl butylcarbamate, methyldibromoglutaronitrile, DMDM hydantoin and combinations thereof.

In certain embodiments, the organic acid may be selected from lactic acid, tartaric acid, adipic acid, succinic acid, ascorbic acid, malonic acid, oxalic acid, pyruvic acid, picolinic acid, dipicolinic acid, citric acid, formic acid, acetic acid, propionic acid, other aliphatic or aromatic mono- or poly-carboxylic acids, and combinations thereof. In certain preferred embodiments, the organic acid is lactic acid.

The personal care composition of the present invention includes at least two surfactants. In certain embodiments, surfactant may be any anionic or amphoteric surfactant, or combinations thereof. In certain embodiments, the total amount of active surfactant in the composition is at least 5 weight %. In other embodiments, the total amount of active surfactant is at least 6, 7, 8, 9, 10, 11, 12, 13, 14, or 15 weight %. Under various embodiments, the total amount of active surfactant makes up 5 to 20 weight %, 5 to 15 weight %, 5 to 10 weight % or 5 to 8 weight % of the personal care composition.

A variety of anionic surfactants can be utilized in the personal care composition including, for example, long chain alkyl sulfonates, long chain alkyl phosphates, long chain alkyl alpha olefin sulfonates, long chain alkyl taurates, long chain alkyl isethionates (SCI), long chain alkyl glyceryl ether sulfonates (AGES), sulfosuccinates and the like. In certain embodiments, the anionic surfactant is selected from a taurate; a succinate; a sarcosinate; an isethionate; a carboxylate; a lactylate; glutamate; glycinate; sulfoacetate; and a sulfonate surfactant. These anionic surfactants can be alkoxylated, for example, ethoxylated, although alkoxylation is not required. The alkyl and/or acyl groups of these compounds may comprise from 6 to 30 carbon atoms. In some embodiments, the alkyl and/or acyl groups may comprise from 12 to 28 carbon atoms. These surfactants are typically highly water soluble as their sodium, potassium, alkyl and ammonium or alkanol ammonium containing salt form and can provide high foaming cleansing power. The cation of any anionic surfactant is typically sodium but may alternatively be potassium, lithium, calcium, magnesium, ammonium, or an ion derived from an organic amine.

In certain embodiments, the anionic surfactant is selected from: sodium n-methyl-n-oleyl taurate; sodium cocoyl isethionate; sodium capryloyl isethionate; sodium caproyl isethionate; sodium lauroyl isethionate; sodium palmitoyl isethionate; sodium diisobutyl sulfosuccinate; sodium diamyl sulfosuccinate; di-N-hexyl sodium sulfosuccinate; disodium lauryl sulfosuccinate; disodium laureth sulfosuccinate; disodium PEG-12 dimethicone sulfosuccinate; sodium oleyl sarcosinate; sodium laurate; sodium myristate; sodium palmitate; sodium stearate; sodium lauroyl lactylate; sodium palmitoyl lactylate; sodium stearoyl lactylate; sodium cocoyl glutamate; disodium cocoyl glutamate; sodium lauroyl glycinate; sodium lauryl sulfoacetate; stearyltoluene sodium sulfonate; sodium diamyl sulfosuccinate; sodium pentanesulfonate; a linear alkyl benzene sulfonate (e.g. sodium dodecylbenzenesulfonate or ammonium dodecylbenzenesulfonate); sodium 1-butanesulfonate; sodium lignosulfonate; sodium n-octyl sulfonate; an alpha olefin sulfonate; and a combination of two or more thereof. Other equivalent anionic surfactants may be used. In one embodiment, the anionic surfactant is alpha olefin sulfonate. The alpha olefin sulfonate may include from about 8 to about 20 carbon atoms per molecule ($C_8$-$C_{20}$), about 10 to about 18 carbon atoms per molecule ($C_{10}$-$C_{18}$), about 12 to about 18 carbon atoms per molecule ($C_{12}$-$C_{18}$), or more preferably from about 14 to about 16 carbon atoms per molecule ($C_{14}$-$C_{16}$). In one embodiment, the anionic surfactant is alpha ($C_{14}$-$C_{16}$) olefin sulfonate. In a further embodiment, the anionic surfactant is sodium ($C_{14}$-$C_{16}$) olefin sulfonate.

In other embodiments, the anionic surfactant is one or more anionic surfactants. In certain embodiments, the one or more anionic surfactants can be included in any desired amount necessary to achieve the desired thickening and cleaning properties. In one embodiment, the one or more active anionic surfactants are present in an amount of 1 to about 15% by weight of the total composition. In one embodiment, the one or more active anionic surfactants are present in an amount of about 2 to about 12% by weight of the total composition. In one embodiment, the one or more active anionic surfactants are present in an amount of about 3 to about 10% by weight of the total composition. In one embodiment, the one or more active anionic surfactants are present in an amount of about 3 to about 5% by weight of the total composition.

In at least one embodiment, the personal care composition may be free, or substantially free, of sulfate-containing surfactants. Illustrative sulfate-containing surfactants may be or include, but are not limited to, sodium lauryl sulfate (SLS), ammonium lauryl sulfate (ALS), sodium laureth sulfate (SLES), ammonium laureth sulfate (ALES), or the like. The personal care composition may also be free, or substantially free, of one or more alkylglucosides. Illustrative alkyl glucosides may be or include, but are not limited to, capryl glucoside, decyl glucoside, coco-glucoside, lauryl glucoside, or the like, or combinations thereof. In a preferred implementation, the personal care composition is free, or substantially free, of coco-glucoside and sulfate-containing surfactants.

In certain embodiments, amphoteric surfactants may be used. Suitable amphoteric surfactants include $C_{12-14}$ alkyl betaine; $C_{12-18}$ alkyl betaine; $C_{14-15}$ hydroxysulfo betaine; cocoamidopropyl betaine; cocoamidopropyl sultaine; lauroamphoglycinate; dihydroxyethyl tallow glycinate; isostearoamphopropionate; dodecyl betaine; tetradecyl betaine; hexadecyl betaine; sodium acylamphopropionate; disodium acyldiamphopropionate; sodium lauroamphoacetate; cocoamphodiacetate; $C_{12-18}$ alkylampho propionate; $C_{12}$ alkyliminodipropionate; and any combination thereof. In certain embodiments, the active amphoteric surfactant is present in an amount between 2 to 10 wt. %, 2 to 8 wt. %, 3 to 8 wt. %, or 4 to 8 wt. %, of the total weight of the personal care composition. In other embodiments, the active amphoteric surfactant is present in an amount between 1 to 25 wt. %, 2 to 20 wt. %, 3 to 15 wt. %, or 4 to 10 wt. %, of the total weight of the personal care composition. In certain embodiments, the active amphoteric surfactant is present in an amount of about 20 wt. %, of the total weight of the personal care composition.

In certain embodiments, amphoteric surfactants of betaine may be used. Examples include, but are not limited to, a range of betaines including, for example, high alkyl betaines, such as coco dimethyl carboxymethyl betaine, lauryl dimethyl carboxy-methyl betaine, lauryl dimethyl alpha-carboxyethyl betaine, cetyl dimethyl carboxymethyl betaine, betaineN,N'-dihydroxyethyl-N-ethyl fatty acid ester, lauryl bis-(2-hydroxyethyl)carboxy methyl betaine, stearyl bis-(2-hydroxypropyl)carboxymethyl betaine, oleyl dimethyl gamma-carboxypropyl betaine, and lauryl bis-(2-hydroxypropyl)alpha-carboxyethyl betaine, sulfobetaines such as coco dimethyl sulfopropyl betaine, stearyl dimethyl sulfopropyl betaine, amido betaines, amidosulfobetaines and the like. In further embodiments, betaine-based surfactants may be or include, but are not limited to, imidazoline-based betaines, alkyl dimethyl aminoacetic acid betaines, fatty acid amide propyl betaines, sulfobetaines, or combinations thereof. In a preferred implementation, the betaine-based surfactant may be or include one or more fatty acid amide propyl betaines or fatty acid amidopropyl betaines. Illustrative betaine-based surfactants may be or include, but are not limited to, cocodimethylcarboxymethyl betaine, cocamidopropyl betaine, lauryldimethylcarboxymethyl betaine, lauryldimethylcarboxyethyl betaine, cetyldimethylcarboxymethyl betaine, lauryl-bis-(2-hydroxyethyl)carboxymethyl betaine, oleyldimethylgammacarboxypropyl betaine, lauryl-bis-(2-hydroxypropyl)-carboxyethyl betaine, or the like, or combinations thereof. In a preferred embodiment, the betaine-based surfactant includes cocamidopropyl betaine. Betaines having a long chain alkyl group, particularly coco, may be particularly useful as are those that include an amido groups such as the cocamidopropyl and cocoamidoethyl betaines. The active amphoteric betaine surfactant may be present in an amount ranging from about 2.0 wt. % to about 10.0 wt. % based on the total weight of the personal care composition. In some embodiments, the active amphoteric betaine surfactant may be present in an amount ranging from about 2.0 wt. % to about 8.0 wt. % based on the total weight of the personal care composition. In some embodiments, the active amphoteric betaine surfactant may be present in an amount ranging from about 3.0 wt. % to about 8.0 wt. % based on the total weight of the personal care composition. In some embodiments, the active amphoteric betaine surfactant may be present in an amount ranging from about 4.0 wt. % to about 8.0 wt. % based on the total weight of the personal care composition. In some embodiments, the active amphoteric betaine surfactant may be present in an amount of about 5.0 wt. % based on the total weight of the personal care composition.

In certain embodiments, the weight ratio of amphoteric surfactant to anionic surfactant is from about 0.5:1 to about 6:1, optionally from about 0.55:1 to about 5.8:1, further optionally from about 0.58:1 to about 5.6:1. In certain embodiments, the amphoteric betaine and anionic surfactant are present in a weight ratio of 0.37:0.63 to 0.85:0.15 respectively. In other embodiments, the amphoteric betaine and anionic surfactant are present in a weight ratio of about 0.6:0.4 respectively. In a further embodiment, the amphoteric betaine and anionic surfactant are present in a weight ratio of about 0.5:0.5 respectively.

In further embodiments, the amphoteric surfactant comprises cocamidopropyl betaine and the anionic surfactant comprises an alpha olefin sulfonate.

In certain embodiments, the personal care composition comprises a preservative system comprising an organic acid. The organic acid is selected from: citric acid; lactic acid; acetic acid; formic acid; oxalic acid; uric acid; and malic acid. In certain embodiments, the organic acid is lactic acid. In certain embodiments, the active organic acid is present in an amount of from about 0.3 to about 2 wt. %, from about 0.3 to about 1 wt. %, or from about 0.3 to about 0.8 wt. %.

Lactic acid is a carboxylic acid with the formula $CH_3$-$CH(OH)$—$COOH$. Under one embodiment, the lactic acid is L-(+)-lactic acid or (S)-lactic acid. Under another embodiment the lactic acid is D-(−)-lactic acid or (R)-lactic acid. Under yet another embodiment, the lactic acid is a mixture of the two stereoisomers. In some embodiments, the lactic acid is a mixture of the two stereoisomers comprising at least 80% of L-(+)-lactic acid or (S)-lactic acid. In another embodiment, the lactic acid is a mixture of the two stereoisomers comprising at least 80% of D-(−)-lactic acid or (R)-lactic acid. In some embodiments, the active lactic acid may be present in an amount ranging from about 0.3 wt. % to about 2.0 wt. % based on the total weight of the personal care composition. In some embodiments, the active lactic acid may be present in an amount ranging from about 0.3 wt. % to about 1.0 wt. % based on the total weight of the personal care composition. In some embodiments, the active lactic acid may be present in an amount ranging from about 0.3 wt. % to about 0.8 wt. % based on the total weight of the personal care composition.

In certain embodiments, the personal care composition further comprises sodium benzoate. In some embodiments, the active sodium benzoate may be present in an amount ranging from about 0.1 wt. % to about 1.0 wt. % based on the total weight of the personal care composition. In some embodiments, the active sodium benzoate may be present in an amount ranging from about 0.1 wt. % to about 0.8 wt. % based on the total weight of the personal care composition. In some embodiments, the active sodium benzoate may be present in an amount up to about 1.0 wt. % based on the total weight of the personal care composition. In some embodiments, the active sodium benzoate may be present in an amount up to about 0.8 wt. % based on the total weight of the personal care composition. In some embodiments, the active sodium benzoate may be present in an amount up to about 0.6 wt. % based on the total weight of the personal care composition.

In certain embodiments, the personal care composition further comprises sodium lauroyl sarcosinate. In some embodiments, the active sodium lauroyl sarcosinate may be present in an amount ranging from about 0.2 wt. % to about 1.5 wt. % based on the total weight of the personal care composition. In some embodiments, the active sodium lauroyl sarcosinate may be present in an amount ranging from about 0.4 wt. % to about 1.2 wt. % based on the total weight of the personal care composition. In some embodiments, the active sodium lauroyl sarcosinate may be present in an amount ranging from about 0.4 wt. % to about 1.0 wt. % based on the total weight of the personal care composition.

In certain embodiments, the personal care composition further comprises a humectant. In certain embodiments, the humectant is selected from: glycerin; butyloctanol; hyaluronic acid; urea; sodium lactate; propylene glycol; glycolic acid; sorbitol; and a combination of two or more thereof. In further embodiments, the humectant is selected from glycerin; butyloctanol; and a combination thereof. In some embodiments, the humectant is present in an amount of from about 0.005 wt. % to about 0.5 wt. %, from about 0.01 wt. % to about 0.1 wt. %, or from 0.01 wt. % or 0.05 wt. %. In some embodiments, the active butyloctanol may be present in an amount ranging from about 0.01 wt. % to about 1.0 wt. % based on the total weight of the personal care composition. In some embodiments, the active butyloctanol may be present in an amount ranging from about 0.05 wt. % to about 0.8 wt. % based on the total weight of the personal care composition. In some embodiments, the active butyloctanol may be present in an amount up to 0.4 wt. % wt. % based on the total weight of the personal care composition. In some embodiments, the active butyloctanol may be present in an amount up to 1.0 wt. % wt. % based on the total weight of the personal care composition.

In certain embodiments, the personal care composition is substantially free of thickening polymers. In certain embodiments, the personal care composition is free of thickening polymers.

In certain embodiments, the viscosity of the composition is between about 2000 to about 20000 centipoise (cP). In certain embodiments, the viscosity of the composition is between about 3000 to about 16000 centipoise (cP). In certain embodiments, the viscosity of the composition is between about 4000 to about 12000 centipoise (cP). In certain embodiments, the viscosity of the composition is between about 6000 to about 10000 centipoise (cP). In certain embodiments, the viscosity of the composition is between about 7000 to about 11000 centipoise (cP).

In certain embodiments, the personal care composition has a pH between 3.5 to 10.0. In certain embodiments, the personal care composition has a pH between 3.5 to 6. In certain embodiments, the personal care composition has a pH between 3.75 to 4.5. One of skill in the art may modify the pH according to the particular composition type, for example, in some embodiments, a body wash may have a lower pH than a soap.

In certain embodiments, the personal care composition is substantially free of sulfate containing surfactants. In certain embodiments, the personal care composition is free of sulfate containing surfactants. In certain embodiments, the personal care composition is substantially free of sulfates. In certain embodiments, the personal care composition is free of sulfates.

In certain embodiments, the personal care composition further comprises a cationic polymer. In certain embodiments, the cationic polymer provides conditioning benefits. In certain embodiments, the cationic polymer comprises a copolymer of acrylamide and diallyldimethylammonium chloride. In certain embodiments, the cationic polymer may comprise at least one cellulosic cationic polymer. The cationic cellulose derivatives are well known with the CTFA names, for example, Polyquaternium-4, Polyquaternium-10, Polyquaternium-24, Polyquaternium-67 and Polyquaternium-72 and commercially available from various suppliers under various trade names. Further cationic cellulose derivatives are Polyquaternium-4, Polyquaternium-10, Polyquaternium-24, Polyquaternium-67 and Polyquaternium-72 and more preferred ones are Polyquaternium-4, Polyquaternium-24, Polyquaternium-67 and Polyquaternium-72.

In certain embodiments, the personal care composition further comprises a prebiotic polysaccharide. The prebiotic polysaccharide may comprise a fructan. The prebiotic polysaccharide may comprise inulin. The prebiotic polysaccharide may be present in an amount of about 0.1 wt. % to about 5 wt. %, optionally from about 0.5 wt. % to about 3 wt. %, further optionally about 2 wt. %.

Additional ingredients may be present in the personal care composition. These include water and ingredients to thicken, preserve, emulsify, add fragrance, and color.

In one embodiment, the composition can further comprise certain additives, including, for example, proteins (e.g., hydrolyzed vegetable protein, hydrolyzed wheat protein, hydrolyzed milk protein, hydrolyzed silk and hydrolyzed collagen), vitamins (e.g., panthenol, biotin, vitamin E acetate, vitamin A and D palmitate), moisturizers/humectants (e.g., glycerin, propylene glycol, sodium pyroglutamic acid (also known as PCA), amino acid-based surfactants, and HLA), emollients (e.g., esters, isopropyl myristate, decyl oleate, $C_{12-15}$ alkyl benzoate), oils (e.g., coconut, jojoba, aloe vera, safflower, almond, argon), botanicals (e.g., chamomile, aloe, rosemary), as well as preservatives, dyes, pH adjusters and chelating agents.

In certain embodiments, in order to prevent ingredients from separating, emulsifiers such as diethanolamine may be added. In certain embodiments, additional ingredients may include conditioning agents that moisturize the skin during and after product use. In further embodiments, ingredients, like scent in the form of essential oils or fragrance oils, and colorant in the form of water-soluble dyes may also be used.

In one embodiment, the composition may include vitamins, including but not limited to, tocopherol, retinol, and ascorbic acid. In one embodiment, the composition may include vitamin derivatives such as ascorbyl monopalmitate, tocopheryl acetate, and Vitamin E palmitate. In one embodiment, the composition may include vitamins and vitamin derivatives.

In certain embodiments, the personal care compositions of the present invention may comprise a blend of short chain fatty acids ("SCFA") comprising a plurality of short chain fatty acids. Optionally, the personal care composition may further comprise a short-chained alcohol or a polyol.

The personal care composition of the present invention may further comprise a structure agent. The structure agent imparts a structure effect to the hair treated with the conditioner composition—i.e., imparts body to the hair. The structure agent may be ionic. The structure agent may be cationic.

The structure agent may comprise a polysaccharide. The polysaccharide may be cationic. The structure agent may be selected d from one or more of: cationic guar gum, cationic cellulose, cationic callose, cationic xylan, cationic mannan, cationic galactomanna n, and derivatives thereof. Cationic polysaccharides may include cationic polysaccharides that may be obtained by the use of different possible cationic etherifying agents, such as for example the family of quaternary ammonium salts.

In a non-limiting embodiment, the guar gums may be polysaccharides composed of the sugars galactose and mannose. The backbone is a linear chain of β 1,4-linked mannose residues to which galactose residues are 1,6-linked at every second mannose, forming short side-branches.

In the case of cationic polysaccharides such as cationic guars, the cationic group may be then a quaternary ammonium group bearing 3 radicals, which may be identical or different, preferably chosen from hydrogen, alkyl, hydroxyalkyl, epoxy alkyl, alkenyl, or aryl, preferably containing 1 to 22 carbon atoms, more particularly 1 to 14 and advantageously 1 to 3 carbon atoms. The counterion is generally a halogen, which is one embodiment is chlorine.

In some embodiments, the cationic polysaccharides may be selected from trimethylamino(2-hydroxyl)propyl, with a counter ion. Various counter ions can be utilized, including but not limited to halides, such as chloride, fluoride, bromide, and iodide, sulfate, methylsulfate, and mixtures thereof.

Cationic guars of the present invention may be chosen from one or more of cationic hydroxyalkyl guars, such as cationic hydroxyethyl guar (HE guar), cationic hydroxypropyl guar (HP guar), cationic hydroxybutyl guar (HB guar), and cationic carboxylalkyl guars including cationiccarboxymethyl guar (CM guar), cationic alkylcarboxy guars such as cationic carboxylpropyl guar (CP guar) and cationic carboxybutyl guar (CB guar), carboxymethylhydroxypropyl guar (CMHP guar).

The structuring agent may be present in an amount ranging from about 0.1 wt. % to about 0.5 wt. % based on the total weight of the personal care composition. In some embodiments, the structuring agent is present in an amount ranging from about 0.2 wt. % to about 0.4 wt. % based on the total weight of the personal care composition. In some embodiments directed to improved smoothness, the structuring agent is present in an amount of about 0.3 wt. % based on the total weight of the personal care composition. In some embodiments directed to improved foaming, the structuring agent is present in an amount of about 0.1 wt. % based on the total weight of the personal care composition.

The personal care composition of the present invention may further comprise skin compatible oils within the composition. Skin compatible oils include a range of liquid hydrocarbons, for example, linear and branched oils such as liquid paraffin, squalene, squalane, mineral oil, low viscosity synthetic hydrocarbons such as polyalphaolefins, commercially available from ExxonMobil under the trade name PURESYN PAO and polybutene under the trade name PANALANE™ or INDOPOL™. Light (low viscosity) highly branched hydrocarbon oils may also be suitable in some instances. Other useful skin compatible oils may be silicone based, for example, linear and cyclic polydimethyl siloxane, organo functional silicones (alkyl and alkyl aryl), and amino silicones.

In other embodiments, the composition may include any of following materials in any desired amount to achieve a desired effect in the composition (amounts that can be used in some embodiments are provided): one or more alkaline salts, for example, sodium chloride, sodium sulfate, sodium carbonate, sodium bicarbonate and/or their equivalents (0 to 5% by weight); foaming agents, for example decyl glucoside, and/or their equivalents (0 to 3% by weight); glyceryl esters and derivatives, for example glycol distearate, and/or their equivalents (0 to 3%; by weight); sequestrants, for example, tetrasodium EDTA, and/or their equivalents (0 to 2% by weight); biocides, for example, Triclosan (2,4,4'-trichloro-2'-hydroxydiphenyl ether), DMDM hydantoin, formaldehyde and/or imidazolidinyl urea, and/or their equivalents (0 to 2% by weight); organic acids, for example, citric acid and/or formic acid and/or their equivalents (0 to 2% by weight); viscosity modifiers (0 to 2% by weight); fragrances and/or perfumes (0 to 5% by weight); preservatives, for example, phenoxyethanol, formaldehyde solution, parabens, pentanediol or sorbic acid (0 to 2% by weight); pearlizing agents, for example, glycol distearic esters, such as ethylene glycol distearate, but also fatty acid monoglycol esters (0 to 3% by weight); stabilizers, for example, metal salts of fatty acids, such as e.g. magnesium stearate, aluminum stearate and/or zinc stearate (0 to 2% by a weight); and dyes and pigments that are approved and suitable for cosmetic purposes.

In certain embodiments, microbeads may be added to the personal care composition. Microbeads are microspheres that may added to a variety of cosmetic products for their exfoliating qualities.

Personal care composition may also contain the ingredient menthol, which gives a cooling and stimulating sensation on the skin, and some men's shower gels are also designed specifically for use on hair and body. Shower gels contain milder surfactant bases than shampoos, and some also contain gentle conditioning agents in the formula. This means that shower gels can also double as an effective and perfectly acceptable substitute to shampoo, even if they are not labelled as a hair and body wash. Washing hair with shower gel should give approximately the same result as using a moisturizing shampoo The personal care composition may further comprise one or more fragrances. The fragrance may be present in an amount ranging from about 0.01% wt. % to about 2.0% wt. %—based on the total weight of the soap composition—including all percentages and sub-ranges there-between. Each particle may be formed entirely of the soap composition—therefore, the weight percentages referred to here may also be in reference to the total weight of the respective particle. In some embodiments, the fragrance may be present in an amount ranging from about 0.4% wt. % to about 1.7% wt. %—based on the total weight of the soap composition-including all percentages and sub-ranges there-between.

Non-limiting examples of fragrances and perfumes include odor compounds selected from: 7-acetyl-1,2,3,4,5, 6,7,8-octahydro-1,1,6,7-tetramethylnaphthalene, α-ionone, β-ionone, γ-ionone α-isomethylionone, methylcedrylone, methyl dihydrojasmonate, methyl 1,6,10-trimethyl-2,5,9-cyclododecatrien-1-yl ketone, 7-acetyl-1,1,3,4,4,6-hexamethyltetralin, 4-acetyl-6-tert-butyl-1,1-dimethylindane, hydroxyphenylbutanone, benzophenone, methyl β-naphthyl ketone, 6-acetyl-1,1,2,3,3,5-hexamethylindane, 5-acetyl-3-isopropyl-1,1,2,6-tetramethylindane, 1-dodecanal, 4-(4-hydroxy-4-methylpentyl)-3-cyclohexene-1-carboxaldehyde, 7-hydroxy-3,7-dimethyloctanal, 10-undecen-1-al, isohexenylcyclohexylcarboxaldehyde, formyltricyclodecane, condensation products of hydroxycitronellal and methyl anthranilate, condensation products of hydroxycitronellal and indole, condensation products of phenylacetaldehyde and indole, 2-methyl-3-(para-tert-butylphenyl) propionaldehyde, ethylvanillin, heliotropin, hexylcinnamaldehyde, amylcinnamaldehyde, 2-methyl-2-(isopropylphenyl) propionaldehyde, coumarin, γ-decalactone, cyclopentadecanolide, 16-hydroxy-9-hexadecenoic acid lactone, 1,3,4,6,7,8-hexahydro-4,6,6,7,8,8-hexamethylcyclopenta-γ-2-benzopyran, β-naphthol methyl ether, ambroxane, dodecahydro-3α,6,6,9α-tetramethylnaphtho[2,1b]furan, cedrol, 5-(2,2,3-trimethylcyclopent-3-enyl)-3-methylpentan-2-ol, 2-ethyl-4-(2,2,3-trimethyl-3-cyclopenten-1-yl)-2-buten-1-ol, caryophyllene alcohol, tricyclodecenyl propionate, tricyclodecenyl acetate, benzyl salicylate, cedryl acetate, and tert-butylcyclohexyl acetate.

Other fragrances may include odor compounds selected from essential oils, resinoids and resins from a large number of sources, such as, for example, Peru balsam, olibanum resinoid, styrax, labdanum resin, nutmeg, *cassia* oil, benzoin resin, coriander, and lavandin.

Further suitable fragrances include odor compounds selected from phenylethyl alcohol, terpineol, linalool, linalyl acetate, geraniol, nerol, 2-(1,1-dimethylethyl)cyclo-hexanol acetate, benzyl acetate, and eugenol. The fragrances or perfumes can be used as single substances or in a mixture with one another.

The personal care composition may further comprise one or more colorants. The colorants may be a pigment, a dye, or mixtures thereof. Non-limiting examples of pigments include titanium dioxide, Zinc Oxide, Kaolin, Mica etc. Non-limiting examples of dyes include food dyes suitable for food, drug and cosmetic applications, and mixtures thereof. Some color agents (colorants) are known as FD&C dyes.

The colorants may be present in an amount ranging from about 0.0001% wt. % to about 0.4% wt. %—based on the total weight of the soap composition—including all percentages and sub-ranges there-between. Each particle may be formed entirely of the soap composition—therefore, the weight percentages referred to here may also be in reference to the total weight of the respective particle. In some embodiments, the colorants may be present in an amount ranging from about 0.0001% wt. % to about 4% wt. %—based on the total weight of the personal care composition—including all percentages and sub-ranges there-between.

The personal care composition may comprise a silicon-containing component. The silicon-containing component may comprise one or more silicone oils, such as dimethicone. Dimethicone is a mixture of fully methylated linear siloxane polymers end blocked with trimethylsiloxy units. Dimethiconol is a dimethyl silicone polymer terminated with hydroxyl groups. These silicone oils are relatively non-volatile liquids.

The silicone oil may be copolymer, such as dimethicone-copolyol. Dimethicone-copolyol may comprise one or more copolymer of dimethylpolysiloxane with polyoxyethylene and/or polyoxypropylene side chains. The copolymer may alternatively comprise phosphated silicone polymers of the above-cited patent can be called dimethicone copolyol phosphates. In terms of chemical structure, the phosphate group forms the terminus of the polyoxyalkylene side chain, and the end hydroxyl has been converted to an ester linkage to the phosphate group.

In a non-limiting embodiment, the dimethicone copolyol may be selected from the:

$$(CH_3)_3SiO\!-\!\!\left[Si(CH_3)_2O\right]_x\!\!-\!\!\left[\begin{array}{c}CH_3\\|\\Si\!-\!O\\|\\C_3H_6\\|\\O\\|\end{array}\right]_y\!\!-\!\!Si(CH_3)_3$$
$$(C_2H_4O)_a(C_3H_6O)_b\!-\!H$$

wherein x is equal to from about 3 to about 30, y is equal to from about 1 to about 10, a is equal to from 0 to about 100, and b is equal to from 0 to about 100, wherein at least one of either a or b is greater than 0 and wherein the HLB value is about 14 or less.

The dimethicone copolyols may comprise have the structure:

$$R\!-\!O\!-\!(C_3H_7O)_y\!-\!(C_2H_4O)_x\!-\!(CH_2)_3\!-\!\underset{\underset{CH_3}{|}}{\overset{\overset{CH_3}{|}}{Si}}\!-\!O\!\left[\underset{\underset{CH_3}{|}}{\overset{\overset{CH_3}{|}}{Si}}\!-\!O\right]_m\!\underset{\underset{CH_3}{|}}{\overset{\overset{CH_3}{|}}{Si}}\!-\!(CH_2)_3\!-\!(OC_2H_4)_x\!-\!(OC_3H_7)_y\!-\!O\!-\!R$$

wherein the R group is hydrogen or methyl, wherein x is equal to from 0 to about 100, y is equal to from 0 to about 100, and m is equal to from about 1 to about 75, wherein at least one of either x or y is greater than 0, and wherein the HLB value is about 14 or less, The silicon-containing component may be present in an amount ranging from 0.5 wt. % to about 2.0 wt. %—including all amounts and sub-ranges there-between—based on the total weight of the personal care composition. In some embodiments, the silicon-containing component may be present in an amount ranging from about 0.5 wt. % to about 1.5 wt. %—including all amounts and sub-ranges there-between—based on the total weight of the personal care composition. In some embodiment. In some embodiments directed to improved smoothness, the structuring agent is present in an amount of about 0.8 wt. % based on the total weight of the personal care composition. In some embodiments directed to improved foaming, the structuring agent is present in an amount of about 0.5 wt. % based on the total weight of the personal care composition.

The composition of the present invention may comprise a carrier. The carrier may be a liquid carrier. The carrier may be predominantly water, but organic solvents also can be included in order to facilitate manufacturing of the composition or to provide esthetic properties, such as viscosity control. Non-limiting examples of suitable solvents include the lower alcohols like ethyl alcohol and isopropyl alcohol; glycol ethers, like 2-butoxyethanol, ethylene glycol mono-ethyl ether, propylene glycol and diethylene glycol mono-ethyl ether or monomethyl ether; and mixtures thereof. Non-aqueous solvents can be present in the conditioner composition of the present invention in an amount of about 1% to about 50%, and in particular about 5% to about 25%, by weight of the total weight of the carrier in the composition.

The carrier may comprise water. Water may be included in the composition. Water can be included in an amount of 0 to about 90% by weight. In one embodiment, water is present at about 50% to about 90% by weight. In one embodiment, water is present at about 50% to about 70% by weight. The water may be soft water. The term "soft water" refers to water having a low concentration of ions, specifically, calcium and magnesium ions. For example, soft water is water having less than about 60 mg/l calcium carbonate, preferably less than 50 mg/l of calcium carbonate. The carrier may comprise 100 wt. % of water—specifically soft water. In other embodiments, the carrier may be predominantly water—i.e., greater than 50 wt. % water, based on the total weight of the carrier, with the remaining amounts being one or more suitable non-aqueous solvents.

The carrier may be present in an amount ranging from 70.0 wt. % to about 90.0 wt. %—including all amounts and sub-ranges there-between—based on the total weight of the personal care composition. In some embodiments, the carrier component may be present in an amount ranging from about 75 wt. % to about 85 wt. %—including all amounts and sub-ranges there-between—based on the total weight of the personal care composition. In some embodiments directed to improved smoothness, the carrier may be present in an amount of about 81 wt. % to about 83 wt. % based on the total weight of the personal care composition. In some embodiments directed to improved foaming, the carrier may be present in an amount of about 79 wt. % to about 81 wt. % based on the total weight of the personal care composition.

In some embodiments, the personal care compositions described herein are in a form selected from: a hand soap; a gel; a shampoo; a conditioner; a cleanser; and a scrub (e.g. an exfoliating scrub or a facial scrub). In some embodiments, the personal care composition is selected from: a hand soap, a body wash, a shower gel, a shampoo, a conditioner, a cleanser, an exfoliating scrub, and a facial scrub.

The present invention is also directed to a method of method of forming a personal care composition, wherein the method comprises mixing: a cosmetically acceptable carrier; a preservative system comprising an organic acid; and a sulfate-free surfactant system comprising: an anionic surfactant; and an amphoteric surfactant. In some embodiments of the method, the anionic surfactant is alpha olefin sulfonate. In some embodiments of the method, the amphoteric surfactant is cocamidopropyl betaine. In some embodiments of the method, the organic acid is lactic acid. In some embodiments of the method, the weight ratio of cocamidopropyl betaine to alpha olefin sulfonate is between 0.37: 0.63 to 0.85:0.15. In some embodiments of the method, the alpha olefin sulfonate is present between 1 to 15%, 2 to 12%, or 3 to 10% by weight. In some embodiments of the method, the cocamidopropyl betaine is present in an amount between 2 to 10%, 2 to 8%, 3 to 8%, or 4 to 8% by weight. In some embodiments of the method, the lactic acid is present at about between 0.3 to 2%, 0.3 to 1%, or 0.3 to 0.8% by weight of the composition. In some embodiments of the method, the method further comprises sodium benzoate. In some embodiments of the method, the sodium benzoate is present up to about 0.8% by weight.

In some embodiments of the method, the method further comprises sodium lauroyl sarcosinate. In some embodiments of the method, the sodium lauroyl sarcosinate is present between 0.2 to 1.5% by weight. In some embodiments of the method, the method further comprises butyloctanol. In some embodiments of the method, the butyloctanol is present up to about 0.4% by weight. In some embodiments of the method, the composition is free of thickening polymers. In some embodiments of the method, the pH of the composition is between 3.5 to 6.5. In some embodiments of the method, the viscosity of the composition is between 4000-12000 centipoise (cP). In some embodiments of the method, the composition is free of sulfate. In some embodiments of the method, the personal care composition is selected from: a hand soap, a body wash, a shower gel, a shampoo, a conditioner, a cleanser, an exfoliating scrub, and a facial scrub.

The present invention is also directed to a method of cleansing a keratinous substance comprising applying a personal care composition according to any one of embodiments described to the skin of a subject in need thereof. The spreading of the personal care composition may be done by hand, or it may be done by an instrument such as a glove or a piece of cloth. In certain embodiments of the method, the keratinous surface is selected from: skin, hair; nails; and a combination of two or more thereof. In certain embodiments of the method, the method further comprises rinsing the skin to which the personal care composition was applied.

The method of applying the personal care composition may leave behind a film. The thickness of the film depends on other parts of the formulation, but for a lotion, the thickness will be comparable to the thicknesses of other lotions, body washes, or deodorants. For those embodiments wherein the personal care composition is a lotion, the thickness is about 50 μm.

In some embodiments, the present invention is also directed to a method of treating, preventing or ameliorating a symptom associated with a disease, disorder or condition of a keratinous substance, comprising applying a personal care composition according to any one of the embodiments described herein to a keratinous substance of a subject in need thereof. In some embodiments, the disease, disorder or condition of a keratinous substance is selected from: dandruff; dry scalp; and staining or damage caused by pollution. The present invention is also directed to a method of cleansing a keratinous substance comprising applying a personal care composition according to any of the embodiments provided herein to a keratinous substance of a subject in need thereof. In certain embodiments, the keratinous substance is selected from: skin, hair, nails, and a combination of two or more thereof. In certain embodiments, the method further comprises rinsing the personal care composition from the keratinous substance to which it is applied.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Example 1

Zero-shear viscosity analysis was performed on various compositions having mixed micelles of CAPB/AOS having a total concentration of 200 mM (6.5% to 6.7% active ingredient) and at pH 3.5. When the CAPB fraction was increased from 0.5 to 0.6, the solution viscosity rose from 1 Pascal-second (Pas) to 180 Pas, with any further increase of the CAPB fraction resulting in a viscosity drop. Further analysis was made to characterize the impact of other ingredients on zero-shear viscosity of mixtures containing 200 mM CAPB/AOS with molar ratios of 0.6/0.4 respectively at pH 4.0. Table 1 summarizes these results.

TABLE 1

| Ingredient | Zero-Shear Viscosity (Pa · s) |
|---|---|
| Amphoteric Surfactant/Sulfate-free Anionic Surfactant | 0.6 |
| Amphoteric Surfactant/Sulfate-free Anionic Surfactant + 0.1% PEO-PPO Block Copolymer | 0.015 |
| Amphoteric Surfactant/Sulfate-free Anionic Surfactant + 7.5% Humectant 2 | 0.12 |
| Amphoteric Surfactant/Sulfate-free Anionic Surfactant + 2% Fructan | 0.55 |
| Amphoteric Surfactant/Sulfate-free Anionic Surfactant + 0.88% Mixture (Preservative + Moisturizing Agent) | 2 |
| Amphoteric Surfactant/Sulfate-free Anionic Surfactant + 0.2% Skin Conditioning Agent | 7.2 |
| Amphoteric Surfactant/Sulfate-free Anionic Surfactant + 0.5% Fragrance | 45 |
| Amphoteric Surfactant/Sulfate-free Anionic Surfactant + 0.2% Humectant 1 | 600 |

Example 2

Figure 2:
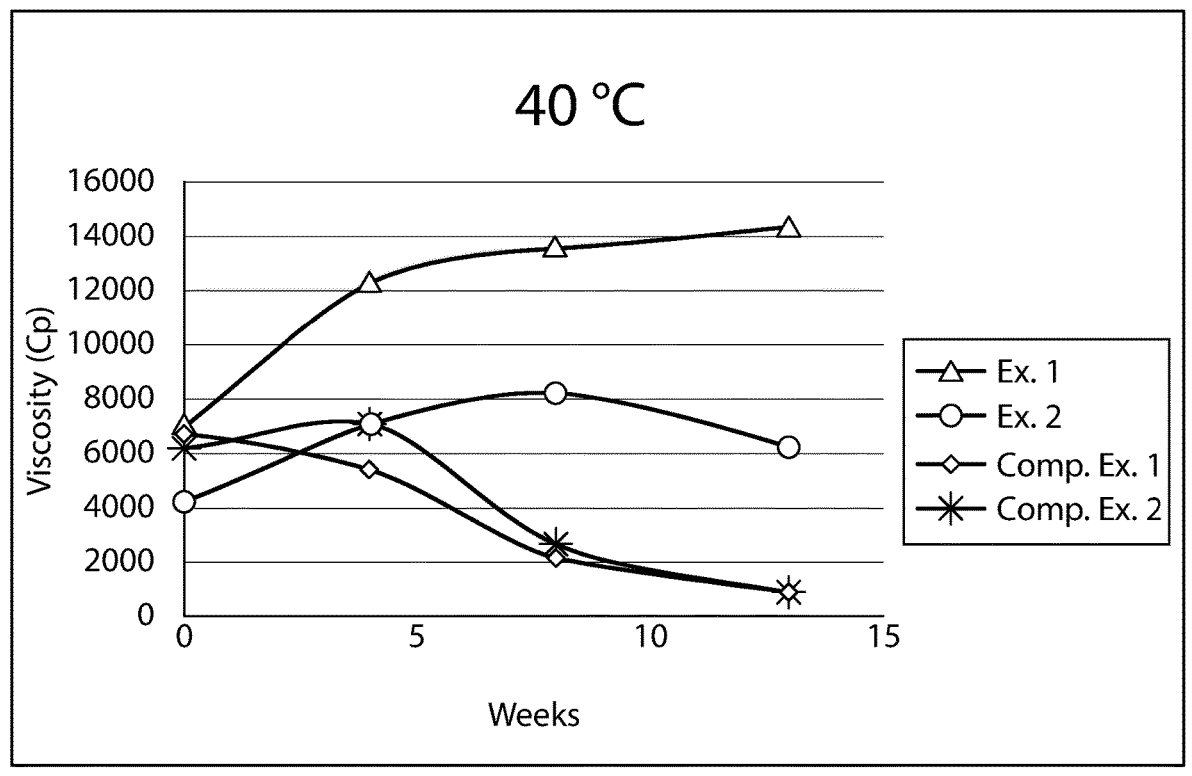
FIG. 2 depicts change in viscosity of various formulations at 40° C. over a period of about 13 weeks.

Further analysis was performed to measure the temperature and time dependent viscosity profile of various formulations. Samples were put in aging chambers either at 25° C. with 60% relative humidity (RH) or at 40° C. with 75% RH for up to 13 weeks. Viscosity was measured at time points 0, 4 weeks, 8 weeks and 13 weeks respectively. Each viscosity point was measured using a Brookfield viscometer RV, spindle 4 at 10 rpm at 25° C.±0.2° C. The composition (as weight % of the entire composition) of these formulations is presented in Table 2. The amphoteric surfactant at 20% w/w corresponds to 6.0% active level. FIG. 1 shows the change in viscosity of these formulations at 25° C. over a period of 13 weeks. FIG. 2 shows the change in viscosity of these formulations at 40° C. over a period of 13 weeks.

TABLE 2

| Ingredient | Ex. 1 | Ex. 2 | Comp. Ex. 1 | Comp. Ex. 2 |
|---|---|---|---|---|
| | Wt. % | | | |
| Water | 63.6367 | 63.1367 | 58 | 58.9439 |
| Edible Oil | 0.1 | 0.1 | 0.1 | 0.1 |
| Amphoteric Surfactant | 20 | 20 | 20 | 20 |
| Humectant | 1.0 | 1.0 | 0.5 | 0.5 |
| Cationic Polymer | 2.2222 | 2.2222 | 2.222 | 2.2222 |
| Pearlizer | — | 0.5 | 1 | — |
| Sulfate-free Anionic Surfactant 1 | 8.9744 | 8.9744 | 12.82 | 12.82 |
| Sulfate-free Anionic Surfactant 2 | 1.6667 | 1.6667 | 3.333 | 3.3333 |
| Preservative | 0.2 | 0.2 | 0.2 | 0.2 |
| Organic Acid (50%) | 1.4 | 1.4 | 1.4 | 1.4 |
| PEO-PPO Block Copolymer | 0.05 | 0.05 | 0.03 | 0.03 |
| Minors | 0.75 | 0.75 | 0.3501 | 0.3501 |

Sulfate free formulas usually require some rheological modifier in order to maintain viscosity, and most formulations tend to drop in viscosity after several days. The four compositions in Table 2 contain no polymeric rheological modifier. FIG. 1 and FIG. 2 respectively, show that the viscosity of the inventive formulations remains constant during the 13 week trial at 25° C. with 60% RH, a good indicator that during the usage of the product, it will remain stable. Surprisingly, even under stressful conditions, 40° C. with 75% RH, exemplary compositions of the present invention (Ex. 1 and Ex. 2) containing less than 11 wt. % anionic surfactant (4.0 wt. % active) are able to maintain rheological stability under high temperature conditions. Evaluations at multiple temperatures is critical to assure that the product will maintain viscosity and/or consistency during the shelf-life and consumer usage.

Example 3

Table 3 describes suitable concentration ranges for exemplary personal care compositions of the present invention. It has been discovered that exemplary compositions of the present invention, encompassed by the formulations reported in Table 3, provide unexpected improvements in viscosity and oil solubilization capacity without the need for a sulfate surfactant or a thickening agent.

TABLE 3

| Ingredient | Wt. % |
|---|---|
| Water | 50-75 (59.48) |
| Preservative | 0.01-1 (0.53-0.6) |
| Sulfate-free Surfactant (e.g., sodium $(C_{14}$-$C_{16})$ olefin sulfonate) | 1-25 (8.9-11.5) |
| Humectant 1 | 0.01-1 (0.15) |
| Amphoteric Surfactant | 1-25 (16-20) |
| Skin Conditioning Agent 1 | 0.05-0.5 (0.1) |
| Organic Acid (50%) | 0.1-2 (1.17-1.547) |
| Humectant 2 | 1-15 (5.1-7.25) |
| Cationic Polymer | 0.01-5 (1) |
| Skin Conditioning Agent 2 | 0.15 |
| Moisturizing Agent | 0.2 |
| Fructan | 2 |
| PEO-PPO Block Copolymer | 0-5 (0.11-0.125) |
| Emollient | 0-5 (0.25) |
| Fragrance | 0.01-1 |

Example 4

Micro robustness (MRT) is a quantitative measurement of the formula's ability to withstand microbial insult. The results encompass the rate of kill of the bacterial inoculum as well as the total kill level. Certain samples are challenged by inoculation with a standard bacterial pool, while other samples are inoculated with specific microorganisms. At selected time intervals, the challenged test material was sampled. Dilutions and platings are then performed to recover the surviving organisms. The log difference in bacterial counts between the product and the inoculum control is then calculated over time. The results are summarized in Tables 4 and 5 (below).

TABLE 4

| | Comp. Ex. 3 | Ex. 3 | Comp. Ex. 4 | Comp. Ex. 5 | Comp. Ex. 6 | Comp. Ex. 7 |
|---|---|---|---|---|---|---|
| | Sulfate-free Anionic Surfactant + PEO-PPO Block Copolymer Preservative System (Wt. %) | | | | | |
| | 0.5 Sodium Benzoate + 0.585 Organic Acid | 0.53 Sodium Benzoate + 0.585 Organic Acid | 0.53 Sodium Benzoate + 0.1 Skin Conditioning Agent + 0.585 Organic Acid | 0.55 Sodium Benzoate + 0.1 Skin Conditioning Agent + 0.585 Organic Acid | 0.6 Sodium Benzoate + 0.1 Skin Conditioning Agent + 0.585 Organic Acid | 0.55 Sodium Benzoate + 0.15 Skin Conditioning Agent + 0.585 Organic Acid |
| pH | 4.21-4.3 | 4.12 | 4.14 | 4.43 | 4.51 | 4.46 |
| MRT | 0.6 | 0.90 | 0.57 | 0.56 | 0.54 | 0.56 |

TABLE 5

| | Ex. 4 | Comp. Ex. 8 | Ex. 5 |
|---|---|---|---|
| | Sulfate-free Anionic Surfactant + PEO-PPO Block Copolymer Preservative System (Wt. %) | | |
| | 0.6 Sodium Benzoate + 0.1 Skin Conditioning Agent + 0.7 Organic Acid | 0.5 Sodium Benzoate + 0.2 Stabilizing Agent + 0.66 Organic Acid | 0.5 Sodium Benzoate + 0.205 Organic Acid 1 + 0.585 Organic Acid 2 |
| pH | 4.01 | 3.95 | 3.77 |
| MRT | 0.98 | 0.65 | 1.03 |

Example 5

Figure 3:
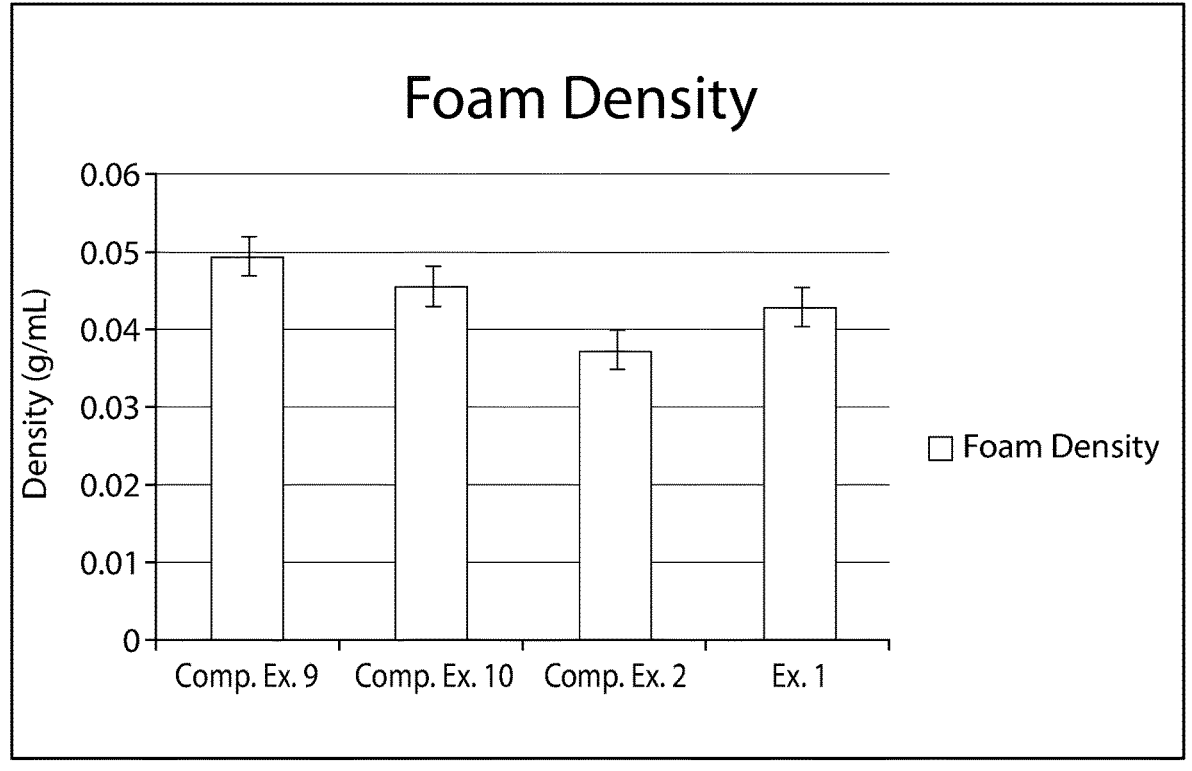
FIG. 3 depicts the results of a foam density analysis of various formulations.

Foam density evaluations are made using a mannequin test. This test utilizes a mannequin head to generate foam while scrubbing one (1) mL of final product for one (1) minute at one hundred (100) beats per minute. Once foam was generated, it was poured in a calibrated pycnometer in order to calculate the density of the foam. Foam density is an important attribute for liquid soap formulations because it represents how creamy or thick the consistency of the foam would be during its application of rubbing onto a surface. The results of these evaluations are depicted in FIG. 3.

Comp. Ex. 9 contains water, cocamidopropyl betaine, coco-glucoside, glycerin, sodium methyl-2-sulfolaurate, sodium benzoate, citric acid, glyceryl oleate, polyquaternium-7, disodium 2-sulfolaurate, parfum, and cetyl betaine.

Comp. Ex. 10 contains water, glycerin, cocamidopropyl betaine, sodium cocoyl glycinate, polyacrylate-33, parfum, phenoxyethanol, stearic acid, sodium lauroyl isethionate, caprylyl glycol, lauric acid, styrene/acrylates copolymer, sodium hydroxide, sodium tallowate, tetrasodium EDTA, sodium isethionate, sodium stearate, etidronic acid, sodium cocoate, and sodium palm kernelate.

Example 6

Figure 4:
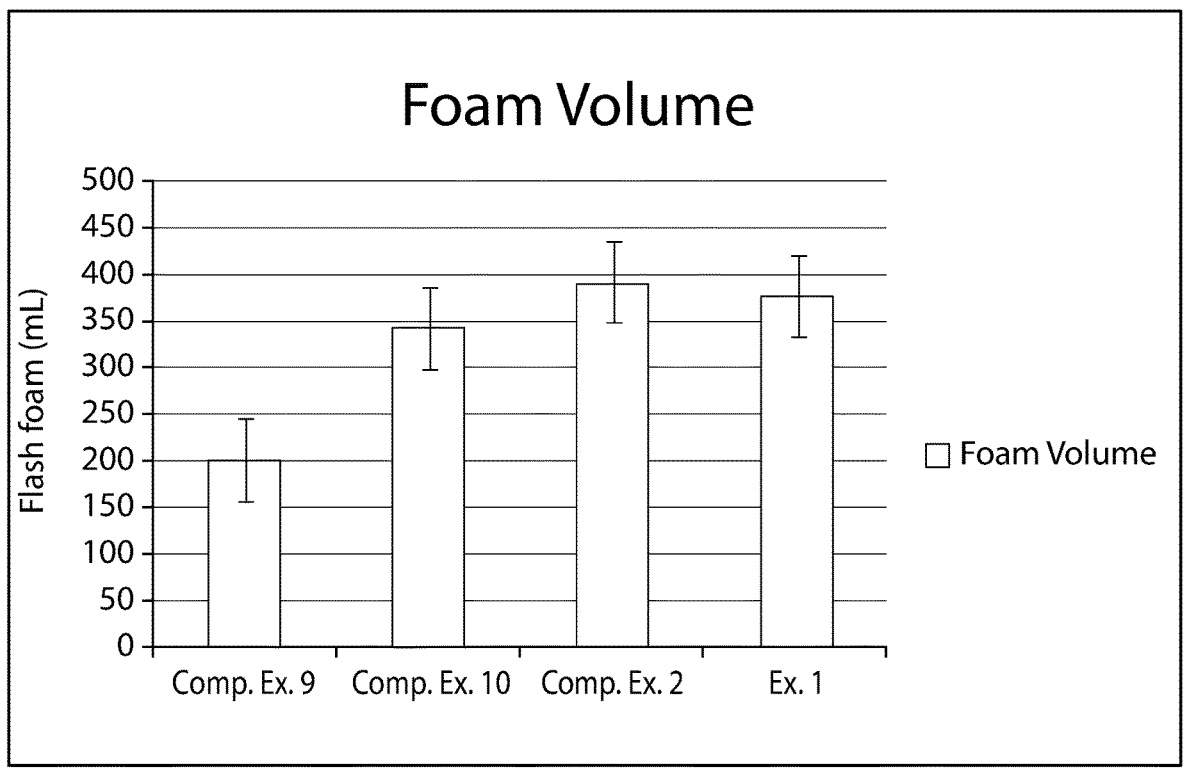
FIG. 4 depicts the results of a foam volume analysis of various formulations.

Foam volume evaluations are conducted using a foam shaker cylinder test, which evaluates how fast a surfactant solution can generate foam at 7 shakes (Flash Foam) and 14 shakes (Maximum Foam). The final products were diluted at 10% w/w with DI water and poured into a 500 mL graduated provette to measure the foam volume generated at RT. This parameter is important because it indicates the foam quantity that would be generated during application of the product. The results of these evaluations are depicted in FIG. 4.

Comp. Ex. 9 contains water, cocamidopropyl betaine, coco-glucoside, glycerin, sodium methyl-2-sulfolaurate, sodium benzoate, citric acid, glyceryl oleate, polyquaternium-7, disodium 2-sulfolaurate, parfum, and cetyl betaine.

Comp. Ex. 10 contains water, glycerin, cocamidopropyl betaine, sodium cocoyl glycinate, polyacrylate-33, parfum, phenoxyethanol, stearic acid, sodium lauroyl isethionate, caprylyl glycol, lauric acid, styrene/acrylates copolymer, sodium hydroxide, sodium tallowate, tetrasodium EDTA, sodium isethionate, sodium stearate, etidronic acid, sodium cocoate, and sodium palm kernelate.

While the present invention has been described with reference to several embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention is to be determined from the claims appended hereto. Further, it will be apparent to those of skill in the art that numerous changes may be made in such details without departing from the spirit and the principles of the invention.

What is claimed is:

1. A personal care composition, comprising:
a cosmetically acceptable carrier;
a preservative system comprising an organic acid; and
a sulfate-free surfactant system comprising:
    an anionic surfactant; and
    an amphoteric surfactant;
wherein the anionic surfactant is present in an amount of from 2% to 12%, and the amphoteric surfactant is present in an amount of from 16% to 20%, based on the total weight of the personal care composition,
wherein the anionic surfactant comprises an alpha olefin sulfonate or sodium (C14-C16) olefin sulfonate;

wherein the amphoteric surfactant comprises cocamidopropyl betaine;
wherein the molar ratio of the amphoteric surfactant to the anionic surfactant is about 1.5:1, wherein the term "about" means +/−5% of the reference value; and
wherein the composition is substantially free of a thickening agent but maintains a viscosity of from about 2,000 centipoise (cP) to about 20,000 cP.

2. The personal care composition according to claim 1, wherein the anionic surfactant further comprises a taurate; a succinate; a sarcosinate; an isethionate; a carboxylate; a lactylate; a glutamate; a glycinate; a sulfoacetate; or a combination of two or more thereof.

3. The personal care composition according to claim 1, wherein the anionic surfactant further comprises sodium n-methyl-n-oleyl taurate; sodium cocoyl isethionate; sodium capryloyl isethionate; sodium caproyl isethionate; sodium lauroyl isethionate; sodium palmitoyl isethionate; sodium diisobutyl sulfosuccinate; sodium diamyl sulfosuccinate; di-N-hexyl sodium sulfosuccinate; disodium lauryl sulfosuccinate; disodium laureth sulfosuccinate; disodium PEG-12 dimethicone sulfosuccinate; sodium oleyl sarcosinate; sodium laurate; sodium myristate; sodium palmitate; sodium stearate; sodium lauroyl lactylate; sodium palmitoyl lactylate; sodium stearoyl lactylate; sodium cocoyl glutamate; disodium cocoyl glutamate; sodium lauroyl glycinate; sodium lauryl sulfoacetate; stearyltoluene sodium sulfonate; sodium diamyl sulfosuccinate; sodium pentanesulfonate; a linear alkyl benzene sulfonate; sodium dodecylbenzenesulfonate; ammonium dodecylbenzenesulfonate); sodium 1-butanesulfonate; sodium lignosulfonate; sodium n-octyl sulfonate; or a combination of two or more thereof.

4. The personal care composition according to claim 1, wherein the amphoteric surfactant further comprises $C_{12\text{-}14}$ alkyl betaine; $C_{12\text{-}18}$ alkyl betaine; $C_{14\text{-}15}$ hydroxysulfo betaine; cocoamidopropyl sultaine; lauroamphoglycinate; dihydroxyethyl tallow glycinate; isostearoamphopropionate; dodecyl betaine; tetradecyl betaine; hexadecyl betaine; sodium acylamphopropionate; disodium acyldiamphopropionate; sodium lauroamphoacetate; cocoamphodiacetate, C12-18 alkylampho propionate; C12 alkyliminodipropionate; or a combination of two or more thereof.

5. The personal care composition according to claim 1, wherein the organic acid is selected from: citric acid; lactic acid; acetic acid; formic acid; oxalic acid; uric acid; and malic acid; and a combination of two or more thereof.

6. The personal care composition according to claim 1, wherein the amphoteric surfactant consists of cocamidopropyl betaine.

7. The personal care composition according to claim 1, wherein the anionic surfactant consists of an alpha olefin sulfonate or sodium ($C_{14}$-$C_{16}$) olefin sulfonate.

8. The personal care composition according to claim 1, wherein the organic acid comprises lactic acid.

9. The personal care composition according to claim 1, wherein the amphoteric surfactant consists of cocamidopropyl betaine; and the anionic surfactant consists of an alpha olefin sulfonate or sodium ($C_{14}$-$C_{16}$) olefin sulfonate.

10. The personal care composition according to claim 1, further comprising a humectant selected from: glycerin; butyloctanol; hyaluronic acid; urea; sodium lactate; propylene glycol; glycolic acid; sorbitol; and a combination of two or more thereof.

11. The personal care composition according to claim 1, having a pH of from about 3.75 to about 4.5.

12. The personal care composition according to claim 1, having a viscosity of from about 3,000 cP to about 16,000 cP.

13. The personal care composition according to claim 1, further comprising a cationic polymer.

14. The personal care composition according to claim 1, further comprising a prebiotic polysaccharide, optionally wherein the prebiotic polysaccharide comprises a fructan, and optionally wherein the prebiotic polysaccharide comprises inulin.

15. The personal care composition according to claim 1, wherein the composition is in a form selected from: a hand soap, a body wash, a face wash, a shower gel, a shampoo, a conditioner, a cleanser, an exfoliating scrub, and a facial scrub.

16. A method of cleansing a keratinous substance comprising applying a personal care composition according to claim 1, to a keratinous substance of a subject in need thereof.

17. The method according to claim 16, wherein the keratinous substance is selected from: skin, hair, nails, and a combination of two or more thereof.

18. The method according to claim 16, further comprising rinsing the personal care composition from the keratinous substance to which it is applied.

19. The personal care composition according to claim 1, wherein the anionic surfactant is present in an amount of from 8.9% to 11.5%, based on the total weight of the personal care composition.

\* \* \* \* \*